United States Patent [19]

Claremon et al.

[11] Patent Number: 4,677,101

[45] Date of Patent: Jun. 30, 1987

[54] SUBSTITUTED DIHYDROAZEPINES USEFUL AS CALCIUM CHANNEL BLOCKERS

[75] Inventors: David A. Claremon, Norristown; David E. McClure, Lansdale, both of Pa.

[73] Assignee: Merck & Co., Inc., Rahway, N.J.

[21] Appl. No.: 535,502

[22] Filed: Sep. 26, 1983

[51] Int. Cl.$^4$ ............... C07D 491/048; C07D 491/06; C07D 487/12; A61K 31/55

[52] U.S. Cl. .................................... 514/215; 540/580; 540/593; 540/610; 514/929

[58] Field of Search ........... 260/239 BE, 330.9, 245.7; 424/244, 278; 546/321; 514/212, 215; 540/580, 593

[56] References Cited

U.S. PATENT DOCUMENTS 3,441,648 4/1969 Loev et al. ........................... 546/321
3,485,847 12/1969 Bossert et al. ....................... 546/321
4,256,749 3/1981 Horstmann et al. ................. 546/321

OTHER PUBLICATIONS

Gregory et al, Can. J. Chem., vol. 57, pp. 44–52, (1979).
Turchi et al, J. Het. Chem., vol. 17, pp. 1593–1595, (1980).
Anderson et al, J. Chem. Soc. (London), (1965), pp. 2411–2422.
Triggle et al, J. Med. Chem., vol. 23, pp. 1442–1445, (1980).
Henry, The American Journal of Cardiology, vol. 46, pp. 1047–1058, (1980).

*Primary Examiner*—Glennon H. Hollrah
*Assistant Examiner*—D. L. Dinner
*Attorney, Agent, or Firm*—Salvatore C. Mitri; R. Brent Olsen; Michael C. Sudol

[57] ABSTRACT

Substituted dihydroazepines, their preparation, and the use thereof as calcium channel blockers are disclosed.

5 Claims, No Drawings

SUBSTITUTED DIHYDROAZEPINES USEFUL AS CALCIUM CHANNEL BLOCKERS

BACKGROUND OF THE INVENTION

The pharmacological function and importance of calcium antagonists, or calcium channel blockers, is well known and has been extensively reported in the literature [see; e.g., P. D. Henry, "Comparative Pharmacology of Calcium Antagonists: Nifedipine, Verapamil and Diltiazem", *The American Journal of Cardiology*, 46, 1047–1058 (1980); K. H. Dangman, et al., "Effects of Nifedipine on Electrical Activity of Cardiac Cells", *The American Journal of Cardiology*, 46, 1061–1067 (1980); E. Braunwald, "Introduction: Calcium Channel Blockers", *The American Journal of Cardiology*, 46, 1045 (1980); L. D. Hillis, "The New Coronary Vasodilators: Calcium Blockers", *J. Card. Med.*, 5(6), 583 (1980); M. J. Berridge, "Receptors and Calcium Signalling", *Trends in Pharmacological Sciences* 1, 419, (1980); W. G. Nayler, et al., "Calcium Antagonists: definition and mode of action", *Basic Research in Cardiology*, 76, No. 1, 1–15 (1981)].

Dihydropyridines have been employed to prepare dihydroazepines. For example, Anderson, et al. [J. Chem. Soc., 2411 (1965)] disclose solvolysis of esters of dihydropyridines to obtain alkoxy dihydroazepines, and Turchi, et al. [*J. Heterocyclic Chem.*, 17, 1593–95 (1980)] disclose the preparation of 4,5-dihydroazepines via mesoionic oxazolium 5-oxides by heating primary or secondary α-amino acids in acetic anhydride in the presence of 1,2-dicyanocyclobutene.

SUMMARY OF THE INVENTION

This invention relates to novel substituted dihydroazepines and related compounds which are useful calcium channel blockers and to methods are preparing such compounds. The compounds of this invention can be represented by the general formula:

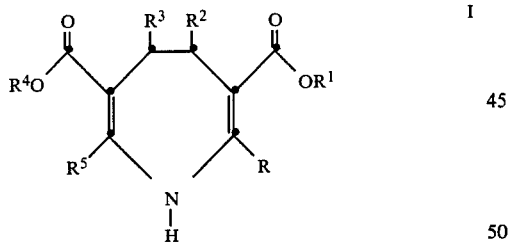

wherein:
$R^1$ and $R^4$ can independently be straight chain and branched loweralkyl or loweralkenyl having up to 8 carbon atoms; cycloalkyl of $C_3$–$C_8$; loweralkyl having up to 8 carbon atoms substituted with 1 to 2 OH groups, $NR^6R^7$ and/or interrupted by 1 to 2 oxygen atoms in the chain wherein $R^6$ and $R^7$ can independently be hydrogen; loweralkyl of $C_1$–$C_8$; aralkyl wherein the aryl group has 6 carbon atoms; or, $R^6$ and $R^7$ with the N atom can be joined together with O, S, SO or $SO_2$ to form a 6-membered ring or with $CH_2$ to form a 5- or 6-membered ring; $R^2$ and $R^3$ can independently be hydrogen provided both $R^2$ and $R^3$ are not hydrogen at the same time; straight chain and branched loweralkyl, loweralkenyl, or loweralkynyl having up to 8 carbon atoms; substituted loweralkyl of $C_1$–$C_8$ wherein the substituent can be trialkylsilyloxy or acyloxy wherein the acyl is derived from a branched or unbranched loweralkanoic acid of $C_2$–$C_8$; cyano provided that when either $R^2$ or $R^3$ is cyano, the other is not hydrogen; $C=ONR^6R^7$ wherein $R^6$ and $R^7$ are as defined above; cycloalkyl of $C_3$–$C_8$; aralkyl wherein the aryl ring contains 6 or 10 carbon atoms and the alkyl contains up to 8 carbon atoms, which aryl group can contain up to three substituents selected from $C_1$–$C_8$ alkyl, $CF_3$, cyano, alkoxy containing up to 8 carbon atoms, nitro, halo (F, Br or Cl), $CONR^6R^7$ wherein $R^6$ and $R^7$ are as defined above; thioalkyl of up to 8 carbon atoms, SO-alkyl of up to 8 carbon atoms, $SO_2$-alkyl of up to 8 carbon atoms; pentafluorophenyl; aryl or substituted aryl wherein the aryl ring contains 6 or 10 carbon atoms and the aryl group can contain up to three substituents selected from $C_1$–$C_8$ alkyl, $CF_3$, cyano, alkoxy containing up to 8 carbon atoms, nitro, halo, (F, Br, or Cl), $CONR^6R^7$ wherein $R^6$ and $R^7$ are as defined above, thioalkyl of up to 8 carbon atoms SO-alkyl of up to 8 carbon atoms, $SO_2$-alkyl of up to 8 carbon atoms; a heteroaryl group of 5–6 atoms containing up to 3 heteroatoms which can be N, O, or S; substituted heteroaryl wherein the heteroaryl ring contains 5–6 atoms and the substituent can be $CF_3$, thioalkyl of up to 8 carbon atoms; benzofused heteroaryl wherein the heterocyclic ring contains 5–6 atoms having up to 3 heteroatoms selected from N, O, or S; or either $R^2$ or $R^3$, together with $R^1$ or $R^4$, respectively, can be joined to form a fused ring as shown in the following structures:

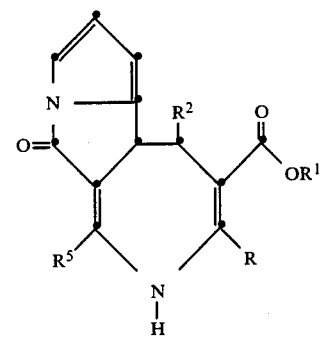

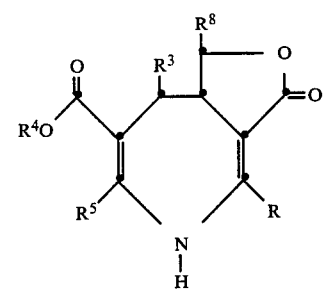

wherein $R_8$ can be hydrogen or loweralkyl of $C_1$–$C_8$; R and $R^5$ can independently be hydrogen; straight chain or branched lower alkyl, alkynyl or alkenyl having up to 8 carbon atoms; hydroxyalkyl of $C_1$–$C_8$; cyano; cycloalkyl of $C_3$–$C_8$; or when R or $R^5$ are hydroxyalkyl they can be respectively joined with either $R^1$ or $R^4$ to form the structure:

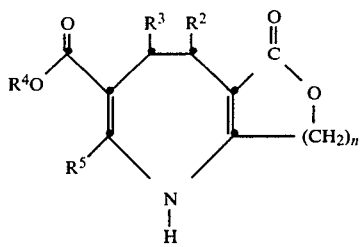

wherein n is 1 or 2.

Preferred compounds of Formula I are those wherein:

$R^1$ and $R^4$ are independently loweralkyl or $NR^6R^7$ substituted loweralkyl;

$R^2$ and $R^3$ are independently hydrogen provided both $R^2$ and $R^3$ are not hydrogen at the same time; pentafluorophenyl; substituted aryl wherein the ring contains 6 or 10 carbon atoms and bears 1–3 substituents selected from alkyl, $CF_3$, cyano, alkoxy, nitro, halo, $CONR^6R^7$ wherein $R^6$ and $R^7$ are as defined above, thioalkyl, SO-alkyl, or $SO_2$-alkyl; acyloxyalkyl; and R and $R^5$ are loweralkyl.

More preferred are those compounds of Formula I wherein:

$R^1$ and $R^4$ are independently loweralkyl or $NR_6R_7$ substituted loweralkyl of $C_1$–$C_8$;

either $R^2$ or $R^3$ is hydrogen and the other is pentafluorophenyl, o- or m-trifluoromethylphenyl; and, R and $R^5$ are methyl.

The products of Formula I can be prepared by the method shown in the following Reaction Scheme wherein R, $R^1$, $R^2$, $R^3$, $R^4$ and $R^5$ are as defined above unless otherwise indicated and X is Cl, Br, I and sulfonate esters such as, for example, methanesulfonate, para-toluenesulfonate, and the like. In the following Reaction Scheme, it should be noted that compound II, when $R^2$=H and X=Cl and when $R^2$=$CH_3$ and X=Cl and, in each instance, $R^1$=$R^4$=$CH_3$ or $C_2H_5$ and R=$R^5$=$CH_3$, are known compounds which can be prepared according to Method C in the Reaction Scheme. [See; e.g., E. Benary, *Chem. Ber.*, 44, 489 (1911)].

REACTION SCHEME

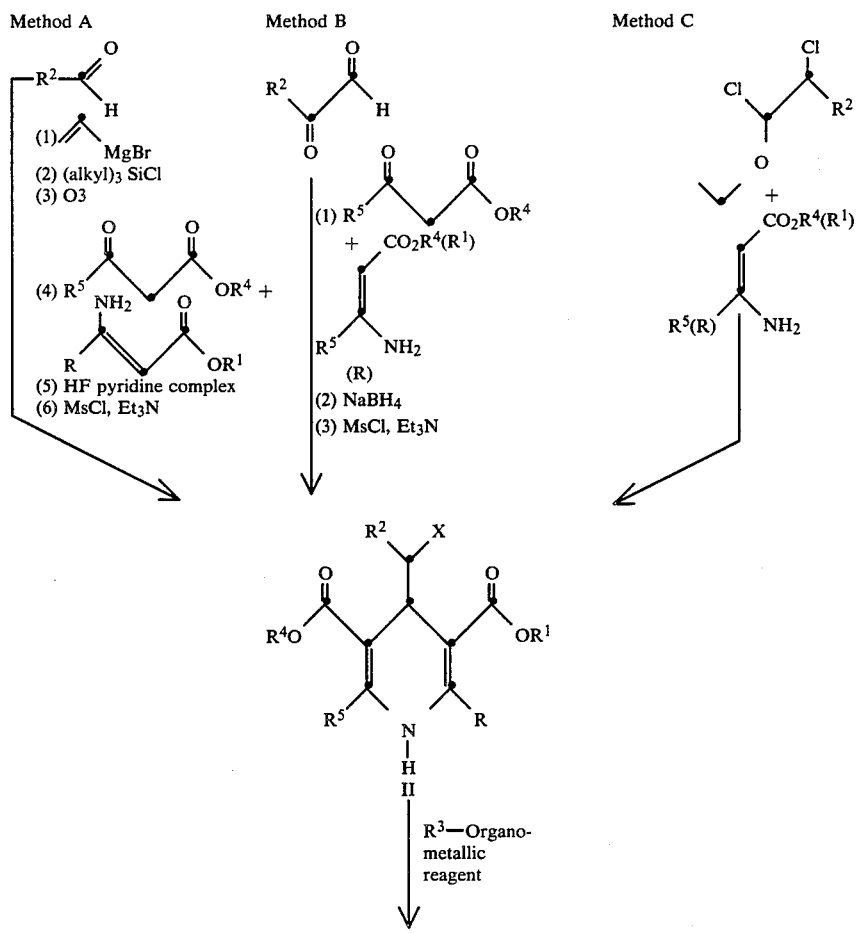

-continued
REACTION SCHEME

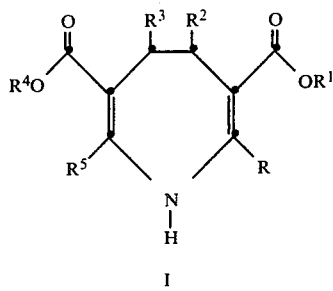

I

In the Reaction Scheme, the applicability of Method B to the synthesis of the desired intermediates (II) depends upon the availability of the required α-keto aldehydes. Many of these aldehydes, particularly when $R^2$=aryl or heteroaryl, can be readily prepared by oxidation, such as with $SeO_2$, and the like, of the corresponding aryl or heteroaryl methyl ketones which are well known in the literature.

The utilization of Method A depends upon the availability of the required aldehydes and numerous, efficient methods for the synthesis of such aldehydes are well known in the literature. The use of aldehydes wherein $R^2$=aryl or heteroaryl are known from such patents as, for example, Belgian Pat. Nos. 710,391; 742,737; 750,139; 760,483; 796,274; 796,278; 845,104; 892,441; European Pat. Nos. 7,293; 9,206; 60,674; Japanese Pat. Nos. 0,032,183; 0,101,365; 6,140,989; 7,118,565; 8,099,181; Netherlands Pat. Nos. 6,803,501; 7,303,134; 7,308,059; 7,401,914; U.S. Pat. Nos. 3,455,939; 3,455,945; 4,258,042; and, West German Pat. Nos. 2,003,146; 2,117,571; 2,210,667; 2,349,538; 2,837,477; 2,847,236; 2,935,772; 2,949,491; 3,022,030.

The alteration of R, $R^1$, $R^4$ and $R^5$ will depend upon the use of substituted 3-aminocrotonates and/or substituted acetoacetates. These are readily available through standard procedures known in the art [see, for example, M. Twanami et al., Chem. Pharm. Bull. 27, 1426 (1979)] and from procedures disclosed in such patents as, for example, Belgian Pat. Nos. 816,157; 843,576; 861,964; 879,263; British Pat. No. 2,026,471; Japanese Pat. Nos. 0,117,778; 2,087,174; 7,031,663; 7,062,258; West German Pat. No. 2,904,552; and, World Pat. No. 8,201,185.

As shown in the foregoing Reaction Scheme, dihydropyridine compound II can be rearranged to the substituted dihydroazepine compound I of the invention by reacting compound II in an inert aprotic organic solvent such as, for example, tetrahydrofuran (THF), toluene, dimethoxyethane, and the like, with about two molar equivalents (Meq) or an organometallic reagent that is useful to promote the formation of carbon-to-carbon bonds; e.g.; Grignard reagents, or other organomagnesium, -copper, -lithium, and the like reagents, but preferably Grignard reagents.

Compounds of Formula I can exist in different isomeric forms such as, for example, threo, erythro, diastereomeric, enantiomeric, and all such forms are included within the scope of this invention.

As indicated above, the calcium channel blocking compounds of this invention have a broad pharmacological spectrum in that they have (i) pronounced and long-lasting vasodilating effect accompanied by an energy-sparing effect on cardiac metabolism; (ii) antiarrhythmic action on cardiac muscle; (iii) vascular spasmolytic action; (iv) antihypertensive action; (v) spasmolytic action on the smooth muscle of the gastrointestinal and urogenital tracts and the respiratory system; (vi) are useful cholesterolaemic and lipidaemic agents and for treating cerebral and peripheral circulatory disorders; and (vii) protect ischemic myocardium. Some of these compounds are also useful cardiotonic agents.

The compounds of the present invention were found to inhibit vascular calcium contraction, reduce cardiac contractile force, inhibit tracheal calcium contraction, inhibit calcium uptake in pituitary cells, and displace tritiated nitrendipine.

The compounds of the present invention can be administered orally, sublingually, or parenterally i.e. intravenously, interperitoneally, etc. and in any suitable dosage form. The compounds can be offered in a form (a) for oral administration e.q. as tablets in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for sublingual administration; e.g., nitroglycerine tablets, lactose tablets, and the like, for rapid dissolution or high molecular weight methylcellulose tablets, carboxymethylcellulose tablets, and the like, for slower, time-releasing delivery; or, (c) for parenteral administration e.g. dissolved or dispersed in a suitable liquid carrier or emulsified. The ratio of active compound to compounding ingredients i.e. carrier, diluent etc. will vary as the dosage form requires. Whatever dosage form is used, the amount of compound of the present invention administered should be sufficient to achieve the pharmaceutical and/or therapeutic effect desired or required in the patient. Generally, doses of the compounds of the invention of from about 300 to about 3000 mg per day may be used, preferably about 500 to about 1500 mg per day. Dosage may be single or multiple depending on the daily total required and the unit dosage. Of course, the dose will vary depending upon the nature and severity of disease, weight of the patient, and other factors which a person skilled in the art will recognize.

It is often advantageous to administer compounds of this invention in combination with angiotensin converting enzyme inhibitors and/or antihypertensives and/or diuretics and/or B-blocking agents. For example, the compounds of this invention can be given in combination with such compounds as enalapril, hydralazine hydrochloride, hydrochlorothiazide, methyldopa, timolol, and the like, as well as admixtures and combinations thereof.

Typically, the individual daily dosages for these combinations can range from about one-fifth of the minimally recommended clinical dosages to the maximum recommended levels for the entities when they are given singly. Naturally, these dose ranges can be adjusted on a unit basis so necessary to permit divided daily dosages and, as noted above, the dose will vary depending on the nature and severity of the disease, weight of patient, special diets and other factors.

DETAILED DESCRIPTION OF THE INVENTION

The following Examples are provided to further illustrate the best mode currently known for obtaining the compounds of the invention, but are not to be construed as being limitative of the invention. Unless otherwise indicated, all temperatures are in °C.

Example 1

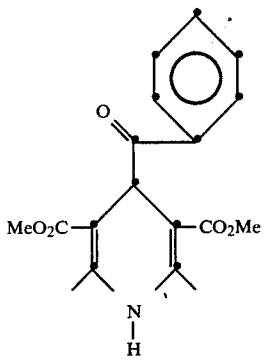

1

Phenyl glyoxal (1.52 g), methyl acetoacetate (1.16 g), and methyl aminocrotonate (1.15 g) were refluxed in 5 ml of isopropyl alcohol for 12 hours. The resulting product was evaporated and chromatographed (silica, 1% MeOH in $CH_2Cl_2$) and gave, upon concentration of appropriate fractions, 0.50 grams of product 1. m.p. 189°–191° C.

Example 2

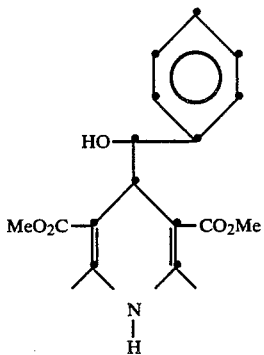

2

To 360 mg. of the ketone 1 in 3 mL of methanol there was added with stirring at 0° C. under argon 40.0 mg of $NaBH_4$. Stirring was continued for 1 hour followed by addition of saturated aqueous sodium potassium tartrate and ethyl acetate. The organic portion was separated and the aqueous phase extracted with 3 more portions of ethyl acetate. The combined organic phases were washed with $H_2O$ and brine, dried ($MgSO_4$), filtered and concentrated to give 350 mg of crude alcohol which was crystallized to give product 2 from $CH_2Cl_2$/hexane. m.p. 179°–181° C.

Example 3

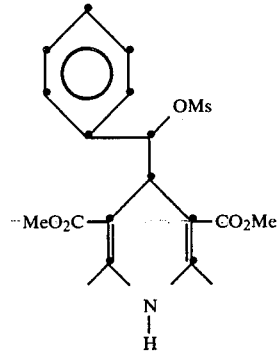

3

To 100 mg of the alcohol 2 in 2.0 mL of dry $CH_2Cl_2$ at −20° C. under argon there was added with stirring 0.186 mL of triethylamine in 3 equal portions followed, after each addition, by 3 equal portions of 0.105 mL of methanesulfonyl chloride. Stirring was continued for an additional ½ hour. The whole was then diluted with ethyl acetate and washed with 5% aqueous sodium bicarbonate and saturated aqueous NaCl. The combined organic extracts were then dried ($MgSO_4$), filtered, and evaporated to give the crude mesylate 3 (100 mgs) IR$\bar{\nu}$=1200 cm$^{-1}$.

Example 4

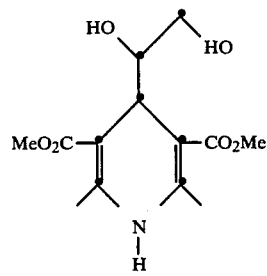

4

Methyl acetoacetate (1.116 g), 1.15 grams of methyl aminocrotonate and 0.90 gram of glyceraldehyde were stirred in 5 mL of THF for 12 hours at 65° C. The whole was then diluted in $CH_2Cl_2$ and washed with saturated aqueous NaCl. The organic phase was dried, ($Na_2SO_4$) filtered, and evaporated. The crude mixture was chromatographed (silica; 10% methanol in $CH_2Cl_2$) to give 280 mg of product 4. NMR$\delta$=4.00 (bd, J=6 Hz, 1H).

Example 5

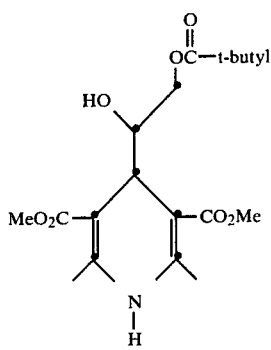

To 280 mg of the diol 4 in 1.0 mL of pyridine with stirring at 0° C. there was added 0.15 mL of pivaloylchloride. After 1 hour at 0° C., the mixture was diluted with CH₂Cl₂ and washed with 1.0N HCl, 5% aqueous NaHCO₃, and brine, then dried (MgSO₄), filtered, and evaporated to give 350 mg of product 5

NMR $\delta=4.20$ (d, J=6.0 Hz, 1H).

Example 6

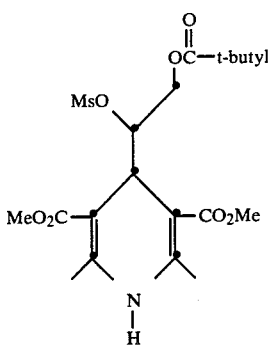

To 350 mg of the pivaloate 5 in 1.5 mL of CH₂Cl₂ at −20° C. under argon there was added 0.21 ml of triethylamine and 0.12 mL of methanesulfonyl chloride. After stirring at −20° C. for 15 minutes, the mixture was diluted with ethyl acetate, and washed with 5% aqueous NaHCO₃, and saturated aqueous NaCl. The organics were dried (MgSO₄) and concentrated to give product 6 (360 mg). This foam was dissolved in dry benzene (20 mL) and concentrated under vacuum.

Example 7

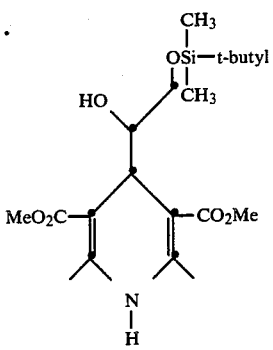

To 359 mg of diol 4 suspended in 2.0 mL of CH₂Cl₂ there was added in sequence 10 mg of N,N-dimethylaminopyridine (DMAP), 0.33 mL of triethylamine, and 190 mg of t-butyldimethyl chlorosilane. After stirring at 25° C. for 6 hours, the reaction was diluted with CH₂Cl₂ and washed with H₂O, 1.0N HCl, saturated aqueous NaHCO₃ and brine. The organic portion was dried (MgSO₄), filtered, and concentrated to give a pale yellow solid which was then triturated with ether to give product 7 (260 mg).

NMR $\delta=4.20$ (bd, J=4.5 Hz, 1H), (90 MHz), (CDCl₃).

Example 8

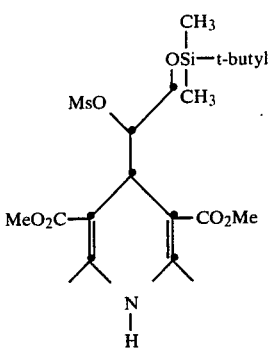

To 500 mg of monosilyl ether 7 in 2.0 mL of CH₂Cl₂ and 0.50 mL of dimethylformamide stirred and cooled to −15° C. there was added 2 aliquots each of triethylamine (0.26 mL) followed by methanesulfonyl chloride (0.145 mL). After 40 minutes, (Temp. −10° C.), the reaction was diluted with CH₂Cl₂ and washed with 1.0N HCl, 5% aqueous NaHCO₃, and brine. The organic portion was dried, filtered and concentrated. Benzene (20 mL) was added and the crude product reconcentrated to give product 8 in a form suitable for subsequent use.

Example 9

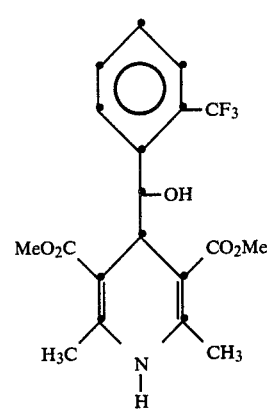

To 43 mL of 1.0M vinyl magnesium bromide solution in THF cooled to −78° C. under an Argon atmosphere there was added dropwise 5.00 grams (3.75 mL) of o-trifluoromethyl benzaldehyde. This was warmed to 0° C. and quenched with saturated aqueous ammonium chloride. The whole was extracted with ethyl acetate, and the organic portion washed with H₂O and brine, then dried (MgSO₄), filtered, and evaporated to a give a crude oily alcohol (5.05 grams).

The crude alcohol was stirred in 25 mL of dry DMF and treated with 5.83 grams of imidazole and 8.90 mL of tert-butyldiphenyl chlorosilane under argon for 18 hrs at 25° C. The mixture was then dissolved in ether and washed with H₂O, 1.2M HCl, 5% NaHCO₃, and brine, then dried (MgSO₄), filtered, and evaporated to give a crude silyl ether 12.65 grams.

The crude silyl ether was dissolved in 200 mL of CH₂Cl₂ and treated with 2 mg of Sudan III. This was cooled to −78° C. and ozone was introduced through a gas inlet tube. The reaction was stopped when the red color of SUDAN III disappeared by bubbling O₂ through and adding 5 mL of dimethyl sulfide. The reaction was allowed to reach 25° C. and washed with H₂O and brine, then dried (MgSO₄), filtered, and evaporated to give a crude aldehyde (12.00 grams)

The crude aldehyde was dissolved in 25 mL of isopropyl alcohol and treated with 3.70 grams of methyl acetoacetate and 3.70 grams of methyl aminocrotonate. The mixture was refluxed for 16 hrs and evaporated to dryness under reduced pressure to give crude dihydropyridine (18.5 grams).

The crude dihydropyridine was dissolved in 200 mL CH₂Cl₂ in a nalgene bottle and stirred at −50° C., pyridinium hydrogen fluoride complex was added and stirring continued for 3 hrs. Saturated aqueous NaHCO₃ was added and the organic portion was separated and washed with 1.2M HCl, H₂O, 5% NaHCO₃, dried (MgSO₄) filtered, and evaporated to give 9 which was recrystallized from ethyl acetatehexane to give a white solid product.

90 MHz'HNMR δ=4.20 (d,J=5.5 Hz, 1H, pyridine C$\underline{H}$) (CDCl₃/DMSOd₆)

Example 10

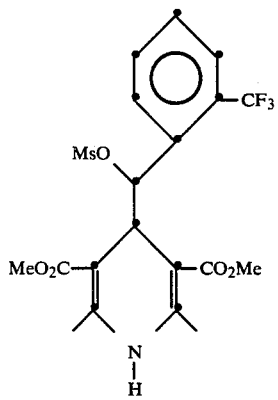

Example 11

Dimethyl-4-phenyl-4,5-dihydro-2,7-dimethyl azepine-3,6-carboxylate

Phenyl magnesium bromide (2.68 mL) in diethylether (3.0M) was added dropwise to 1.00 gram of dimethyl-2,5-dimethyl-4-chloromethyl-1,4-dihydropyridine-3,5-dicarboxylate 11a (3.66 mm) [See; e.g., E. Benary, Chem. Ber., 44, 489 (1911)] in dry tetrahydrofuran under an argon atmosphere at −78° C. Stirring was continued at −78° for 15 minutes followed by warming to −10° C. for 1 hour. The excess Grignard reagent was quenched with saturated aqueous ammonium chloride. Extraction with ethyl acetate (3×75 mL), washing the organic portion with saturated aqueous NaCl, drying (MgSO₄), filtering, and evaporation gave crude product. Crystallization from toluene/hexane (1/1) gave 1.10 gr (92%) of pure dimethyl-4-phenyl-4,5-dihydro-2,7-dimethylazepine-3,6-dicarboxylate (11).

Analysis Calculated: C, 68.55; H, 6.71; N, 4.44; Found: C, 68.68; H, 6.88; N, 4.43; m.p. 135°−7° C.

Examples 12–47

Following the same procedure as described in Example 11 above, additional compounds of Formula I were obtained and are set forth in Table I below showing the organometallic reagents, solvents and temperatures employed and the products obtained. In Table I, the amount of organometallic employed was 2.2 Meq., Ph is phenyl, Ar is aryl, Me is methyl, Ms is mesylate (methansulfonate), Et is ethyl, THF is tetrahydrofuran, and DMSO is dimethylsulfoxide.

Also, in Table I, the Starting Materials are either products 1–11 obtained from the Examples hereinabove or known compounds; i.e., 11b [dimethyl-4-(1-chloroethyl)-1,4-dihydropyridine-3,5-dicarboxylate]. [See, e.g., E. Benary, Chem. Ber., 44, 489 (1911)]. Further, in Table I, unless otherwise indicated, R=R⁵=methyl and R¹=R⁴=methyl.

TABLE I

| | | Products of Formula I | | | |
|---|---|---|---|---|---|
| Example No. | Organometallic Reagent | Starting Material | Solvent(s) | Temp. Range (°C.) | R³ |
| 12 | PhMgBr | 9 | THF/Ether | −78–0 | Ph |
| 13 | Ph₂CuLi | " | Ph/THF/Ether | " | " |
| 14 | Me₂CuLi | " | THF/Ether | " | Me |
| 15 | MeMgBr | " | " | " | " |
| 16 | MeLi | " | Ether | " | " |
| 17 | Vinyl MgBr | " | THF | " | Vinyl |
| 18 | PhCH₂MgCl | " | " | " | PhCH₂ |
| 19 | t-butyl MgCl | " | " | " | t-butyl |
| 20 | cyclohexane MgCl | " | Ether/THF | " | cyclohexyl |
| 21 | n-butyl MgCl | " | " | " | n-butyl |
| 22 | di(n-butyl)Mg | " | " | " | " |

TABLE I-continued

Products of Formula I

| Example No. | Organometallic Reagent | Starting Material | Solvent(s) | Temp. Range (°C.) | R³ |
|---|---|---|---|---|---|
| 23 | naphthyl-MgBr | " | THF | " | naphthyl |
| 24 | 2-CF₃-C₆H₄-MgBr | " | " | " | 2-CF₃-C₆H₄ |
| 25 | 3-CF₃-C₆H₄-MgBr | " | " | " | 3-CF₃-C₆H₄ |
| 26 | 4-CF₃-C₆H₄-MgBr | " | " | " | 4-CF₃-C₆H₄ |
| (b)27 | PhMgBr | 6 | THF/Ether | −78 to −10 | Ph |
| (b)28 | C₆F₅-MgBr | " | THF | −78-0 | C₆F₅ |
| (a)29 | PhMgBr | 8 | THF/Ether | " | Ph |
| (a)30 | C₆F₅-MgBr | " | " | " | C₆F₅ |
| (a)31 | Li-N(Li)-C(=O)-O-t-butyl aryl | " | THF/Pentane | " | aryl-NH-C(=O)-O-t-butyl |

TABLE I-continued

Products of Formula I

| Example No. | Organometallic Reagent | Starting Material | Solvent(s) | Temp. Range (°C.) | R³ |
|---|---|---|---|---|---|
| (a)32 | 3-MeO-C₆H₄-MgBr | " | THF | " | 3-MeO-C₆H₄ |
| (a)33 | 4-MeO-C₆H₄-MgBr | " | " | " | 4-MeO-C₆H₄ |
| (c)34 | C₆F₅-MgBr | 9(c) | THF | " | C₆F₅ |
| (c)35 | 4-CF₃-C₆H₄-MgBr | " | " | " | 4-CF₃-C₆H₄ |
| (d)36 | PhMgBr. | 3 | THF/Ether | " | Ph |
| (d)37 | MeMgBr. | " | THF | " | Me |
| (d)38 | KCN | " | DMSO | room temp. | C≡N |
| 39 | PhMgBr | 11b | THF/Ether | −78-0 | Ph |
| 40 | PhCH₂MgCl | " | THF | " | PhCH₂ |
| 41 | Vinyl MgBr | " | " | " | vinyl |
| 42 | 4-CF₃-C₆H₄-MgBr | " | " | " | 4-CF₃-C₆H₄ |
| 43 | PhLi | " | THF/benzene/Ether | " | Ph |
| 44 | 4-MeO-C₆H₄-MgBr | " | THF | " | 4-MeO-C₆H₄ |

TABLE I-continued

Products of Formula I

| Example No. | Organometallic Reagent | Starting Material | Solvent(s) | Temp. Range (°C.) | R³ |
|---|---|---|---|---|---|
| 45 | cyclohexyl MgCl | 10 | THF/Ether | " | (thiophene-type ring with S) |
| 46 | PhCH₂MgCl (CuI, catalyst) | " | " | " | PhCH₂ |
| 47 | (aryl-MgBr with CF₃) | " | THF | " | (aryl with CF₃) |

$^{(a)}$R² = —CH₂OSi(CH₃)₂(t-butyl)
$^{(b)}$R² = —CH₂OCO(t-butyl)
$^{(c)}$R¹ = R⁴ = -ethyl
$^{(d)}$R² = Ph Physical data for the Formula I compounds shown in Table I are set forth in Table II below:

TABLE II

Physical Data For Products of Formula I

| Example No. | m.p. (°C.) | (e) NMR | IR |
|---|---|---|---|
| 12 | 135–137 | — | — |
| 13 | " | — | — |
| 14 | — | δ = 0.90(d,J − 7 Hz,3H) | — |
| 15 | — | δ = 0.90(d,J − 7 Hz,3H) | — |
| 16 | — | δ = 0.90(d,J − 7 Hz,3H) | — |
| 17 | — | δ = 4.14(bt,J = 6,7 Hz,1H) | — |
| 18 | — | — | ῡ 1690 cm⁻¹ C = OVS |
| 19 | — | δ = 3.25(bd,J = 6 Hz,1H) | — |
| 20 | — | — | ῡ 1680 cm⁻¹ |
| 21 | — | δ = 3.70(s,6H,CO₂Me) | — |
| 22 | — | δ = 3.70(s,6H,CO₂Me) | — |
| 23 | — | δ = 5.55(bd,J = 6 Hz,C—4H) | — |
| 24 | — | δ = 4.77(bd,J = 6H₃,C—4H) | — |
| 25 | — | δ = 5.00(bd,J = 6.0 Hz, C—4H) | — |
| 26 | — | δ = 4.75(bd,J = 6 Hz,C—4H) | — |
| 27 | — | δ = 4.49(bs,1H,ArC<u>H</u>) | — |
| 28 | 62–64 | — | — |
| 29 | — | δ = 4.65(bs,1H,Ar—C<u>H</u>) | — |
| 30 | — | δ = 4.88(db,J = 6 Hz,C4H) | — |
| 31 | — | δ = 4.71(bd,J = 6 Hz) | — |
| 32 | — | δ = 4.64(db,J = 6 Hz) | — |
| 33 | — | δ = 4.77(bd,J = 6 Hz) | — |
| 34 | 112–113 | — | — |
| 35 | 166–167 | — | — |
| 36 | — | δ = 5.07(s,2H,PhC<u>H</u>) | — |
| 37 | — | δ = 4.44(d,J = 6.0 Hz,1H, PhC<u>H</u>) | — |
| 38 | — | δ = 4.75(d,J = 6.0 Hz,1H) | — |
| 39 | 122–122.5 | — | — |
| 40 | — | δ = 3.34(dt,J = 6.0,9.0 Hz, 1H,PhCH₂C<u>H</u>) | — |
| 41 | — | δ = 3.83(m,1H,vinylC<u>H</u>) | — |
| 42 | — | δ = 4.34(bs,1H,PhC<u>H</u>) | — |
| 43 | 122–122.5 | — | — |
| 44 | — | δ = 4.17(bs,1H,ArC<u>H</u>) | — |
| 45 | — | δ = 3.32(dq,J = 9,7 Hz,1H, cyclohexylC<u>H</u>) | — |
| 46 | — | δ = 3.34(dt,J = 6.0,9.0 Hz, 1H,PhCH₂C<u>H</u>) | — |
| 47 | — | δ = 4.58(bs,1H,ArC<u>H</u>) | — |

(e) δ = ppm (multiplicity, coupling in Hz, integration)

Example 48

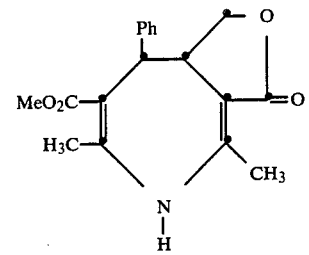

To 65.0 mg of the silyl ether (29) in 0.5 ml of anhydrous THF at 25°, there was added 0.42 mL of 1M tetrabutylammonium fluoride in THF. The mixture was stirred for 12 hours, then diluted with ethyl acetate and saturated aqueous ammonium chloride. The organic layer was separated, washed with water and brine then dried (MgSO₄) and concentrated to give a pale yellow solid.

NMR: δ=4.47 (d, J=3 Hz, 1H, ArC<u>H</u>)

Example 49

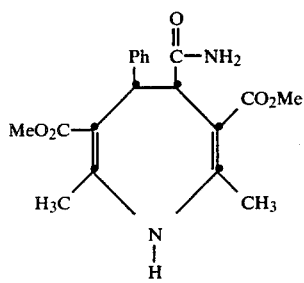

To 130 mg of the nitrile 38 in 2 mL of THF/MeOH (1/1) under an Argon atmosphere at 20° C. there was added 0.76 mL of 1M aqueous NaOH and 0.2 mL of 30% $H_2O_2$ in $H_2O$. After 6 hours of stirring, the whole was cooled to 0° C. and sodium bisulfite was added. The whole was warmed to room temperature and then extracted with ethyl acetate. The organic portion was washed with water and brine, dried over anhydrous $MgSO_4$, filtered, and then evaporated to an oily solid. This solid was chromatographed (silica, 7% methanol in $CH_2Cl_2$) and the appropriate fractions concentrated to give a solid which was then dried over $P_2O_5$ for 15 hours at room temperature.

NMR: δ=4.50 (d, J=6.0 Hz, 1H,

O
‖
CC<u>H</u>)

Example 50

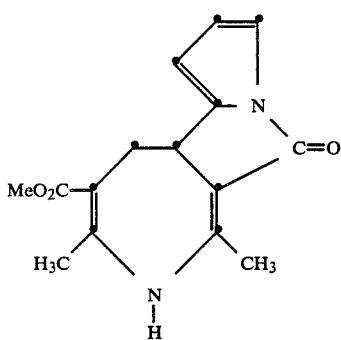

To 18.4 mmol of pyrrole magnesium chloride (generated from pyrrole and MeMgCl at −30° C.) in 20 mL of toluene there was added 1.00 grams of 9 in 10 mL of toluene at −78° C. This was stirred at −78° C. for 1 hr and warmed to −5° C. for 3 hrs. The excess Grignard reagent was quenched with saturated aqueous $NH_4Cl$ and extracted with ethyl acetate. The organic portion was washed with brine then dried ($MgSO_4$), filtered, and evaporated to a crude solid. This solid was recrystalized from ethylacetate-hexane and then from methanol to give 50 as a white solid (500 mg) product.

$^1$H NMR (90 MHz, $CDCl_3$) δ=3.76 (M, 1H, C-4 H).

Example 51

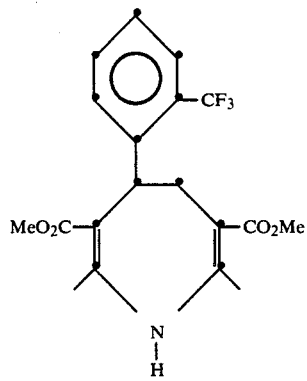

To a hot solution of mesylate 10 in ethanol there can be added guanidine (1.25 m. equiv.) followed by the addition of a large excess of $NaBH_4$ (5 m. equiv.) portionwise at 15 minute intervals over the refluxing time period of 90 minutes. The mixture can then be poured into water and then extracted with $CH_2Cl_2$. After drying ($Na_2SO_4$) and concentration, the product can be crystallized from toluene/hexane to leave 51, the same product as that prepared in Example 25.

Following the same procedures as described in Example 11 above and shown in tabulated Examples 12–47, and using procedures similar to those in Examples 1–10 for preparing the required Starting Materials and as described in connection with Methods A, B and C of the Reaction Scheme, additional compounds of Formula I can be obtained as illustrated in Table III below:

TABLE III
Additional Compounds of Formula I

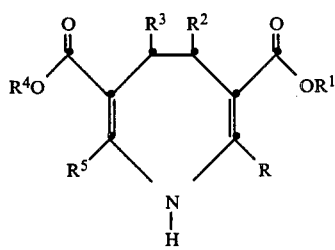

I

| | R | R$^1$ | R$^4$ | R$^3$ | R$^2$ | R$^5$ |
|---|---|---|---|---|---|---|
| a | CH$_3$ | CH$_3$ | CH$_3$ | (2,3, or 4)-C$_6$H$_4$OCH$_3$ | H | CH$_3$ |

TABLE III-continued
Additional Compounds of Formula I

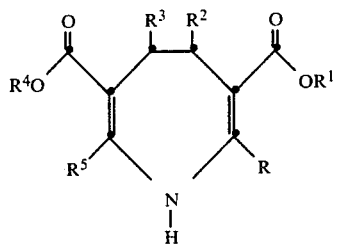

I

| | R | R¹ | R⁴ | R³ | R² | R⁵ |
|---|---|---|---|---|---|---|
| b | " | " | " | (2,3, or 4)-C₆H₄CH₃ | " | " |
| c | " | " | " | H | (3 or 4)-C₆H₄F | " |
| d | " | " c | " | (2,3, or 4)-C₆H₄SCH₃ | H | " |
| e | " | " | H | H | (2,3, or 4)-C₆H₄SO₂CH₃ | " |
| f | " | " | " | " | (2,3, or 4)-C₆H₄Cl | " |
| g | " | CH₂CH₃ | CH₂CH₃ | " | (2,3, or 4)-C₆H₄Br | " |
| h | " | " | " | " | (2,3, or 4)-C₆H₄NO₂ | " |
| i | " | " | " | " | (2,3, or 2,4, or 2,6)-C₆H₃Cl₂ | " |
| j | " | " | " | " | (2,3, or 2,5, or 2,6)-C₆H₃Br₂ | " |
| k | " | " | " | " | (2,3, or 2,5, or 2,6)-C₆H₃F₂ | " |
| l | " | " | CH₃ | " | 3-C₆H₄NO₂ | " |
| m | " | " | CH₃OCH₂CH₂ | " | (2,3)-C₆H₃Cl₂ | " |
| n | " | (CH₃)₂CH | " | " | 3-C₆H₄NO₂ | " |
| o | " | CH₃ | (CH₃)₂CH | " | 3-C₆H₄SO₂CH₃ | " |
| p | " | CH₃(CH₂)₂OCH₂CH₂ | CH₃(CH₂)₂OCH₂CH₂ | 2-C₆H₄SCH₃ | H | " |
| q | " | PhCH₂N(CH₃)CH₂CH₂ | PhCH₂N(CH₃)CH₂CH₂ | H | 3-C₆H₄NO₂ | " |
| r | " | CH₃ | " | " | " | " |
| s | " | CH₂CH₃ | " | " | (2,3)-C₆H₃Cl₂ | " |
| t | " | CH₃ | CH₃ | Ph | 3-C₆H₄NO₂ | " |
| u | " | CH₂CH₃ | CH₂H₃ | " | (2,3)-C₆H₃Cl₂ | " |
| v | " | CH₃ | CH₃ | 3-C₆H₄SCH₃ | 3-C₆H₄NO₂ | " |
| w | " | CH₂CH₃ | CH₂CH₃ | CH₃ | " | " |
| x | " | CH₃ | CH₃ | PhCH₂ | " | " |
| y | " | " | " | 2-C₆H₄CF₃ | CH₂OCOC(CH₃)₃ | " |
| z | " | CH₂CH₃ | CH₂CH₃ | 2,3-C₆F₂H₃ | " | " |
| aa | " | " | " | H | (benzofurazan-yl group) | " |
| bb | " | CH₃ | CH₃ | " | " | CH₂CH₃ |
| cc | CH₂CH₃ | " | " | " | (2,3)-C₆H₃Cl₂ | " |
| dd | " | " | " | " | 3-C₆H₄NO₂ | " |
| ee | CH₃ | " | " | " | " | CH₂OH |
| ff | " | " | " | " | " | CN |
| gg | " | " | PhCH₂N(CH₃)CH₂CH₂ | " | " | CH₃ |

What is claimed is:

1. A compound having the formula:

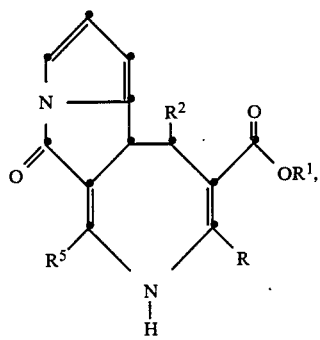

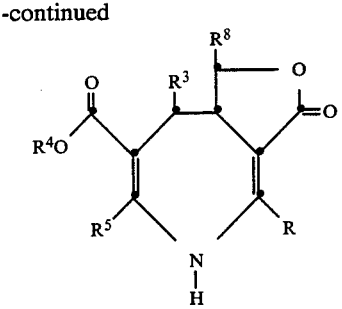

wherein:
R¹ and R⁴ can independently be straight chain and branched loweralkyl or loweralkenyl having up to 8 carbon atoms; cycloalkyl of $C_3-C_8$; loweralkyl having up to 5 carbon atoms substituted with 1 to 2 OH groups, $NR^6R^7$ and/or interrupted by 1 to 2 oxygen atoms in the chain wherein $R^6$ and $R^7$ can independently be hydrogen; loweralkyl of $C_1$-$C_8$; aralkyl wherein the aryl group has 6 carbon atoms; $R^2$ and $R^3$ can independently be hydrogen provided both $R^2$ and $R^3$ are not hydrogen at the same time; straight chain and branched loweralkyl, loweralkenyl, or loweralkynyl having up to 8 carbon atoms; substituted loweralkyl of $C_1$-$C_8$ wherein the substituent can be trialkylsilyloxy or acyloxy wherein the acyl group is derived from a branched or unbranched loweralkanoic acid of $C_2$-$C_8$; $C=ONR^6R^7$ wherein $R^6$ and $R^7$ are as defined above; cycloalkyl of $C_3$-$C_8$; aralkyl wherein the aryl ring contains 6 or 10 carbon atoms and the alkyl contains up to 8 carbon atoms, which aryl group can contain up to three substituents selected from $C_1$-$C_8$ alkyl, $CF_3$, cyano, alkoxy containing up to 8 carbon atoms, nitro, fluoro, bromo or chloro, $CONR^6R^7$ wherein $R^6$ and $R^7$ are as defined above; thioalkyl of up to 8 carbon atoms, SO-alkyl of up to 8 carbon atoms, $SO_2$-alkyl of up to 8 carbon atoms; unsubstituted aryl wherein the ring contains 6 or 10 carbon atoms; pentafluorophenyl; substituted aryl wherein the aryl ring contains 6 or 10 carbon atoms and the aryl group can contain up to three substituents selected from $C_1$-$C_8$ alkyl, $CF_3$, cyano, alkoxy containing up to 8 carbon atoms, nitro, fluoro, bromo or chloro, $CONR^6R^7$ wherein $R^6$ and $R^7$ are as defined above, thioalkyl of up to 8 carbon atoms, SO-alkyl of up to 8 carbon atoms, $SO_2$-alkyl of up to 8 carbon atoms; $R^8$ can be hydrogen or loweralkyl of $C_1$-$C_8$;

R and $R^5$ can independently be hydrogen; straight chain or branched lower alkyl, alkynyl or alkenyl having up to 8 carbon atoms; hydroxyalkyl of $C_1$-$C_8$; cyano or cycloalkyl of $C_3$-$C_8$; or when R or $R^5$ are hydroxyalkyl they can be respectively joined with either $R^1$ or $R^4$ to form the structure:

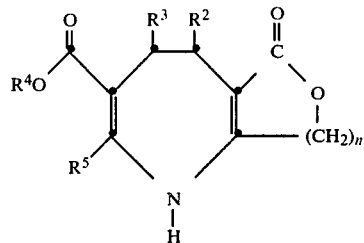

wherein n is 1 or 2.

2. A pharmaceutical composition useful for providing a cardiotonic effect, a vasodilating effect, an antiarrhythmic action on cardiac muscle, vascular spasmolytic action, antihypertensive effect, spasmolytic action on the smooth muscle of the gastrointestinal and urogenital tracts and the respiratory system, cerebral and peripheral circulation and protecting ischemic myocardium which composition consists essentially of a pharmaceutically acceptable carrier and a pharmaceutically effective amount of a compound of claim 1.

3. The composition of claim 2 wherein said pharmaceutical composition includes an additional pharmaceutical agent selected from the group, an angiotensin converting enzyme inhibitor, an antihypertensive, a diuretic, and a β-blocker as well as admixtures and combinations thereof.

4. The composition of claim 3 wherein said additional pharmaceutical agent is selected from the group: enalapril, hydralazine hydrochloride, hydrochlorothiazide, and timolol.

5. A method for providing a cardiotonic effect, a vasodilating effect, an antiarrhythmic action on cardiac muscle, a vascular spasmolytic action, an antihypertensive effect, a spasmolytic action on the smooth muscle of the gastrointestinal and urogenital tracts and the respiratory system, cerebral and peripheral circulation and protecting ischemic myocardium, which method comprises administering to a patient in need of such treatment a pharmaceutically effective amount of a compound of claim 1.

* * * * *